United States Patent [19]

Arnold et al.

[11] Patent Number: 4,817,287
[45] Date of Patent: Apr. 4, 1989

[54] CUTTING TOOL FOR COLOSTOMY WAFER

[76] Inventors: Janet O. Arnold, 1415 Bryant St. Leesburg, Fla. 32749-1211; Shirley H. Sennett, R.R. 1, Box 1283, Fruitland Park, Fla. 32731

[21] Appl. No.: 20,360

[22] Filed: Mar. 2, 1987

[51] Int. Cl.⁴ ............................................. B26F 1/36
[52] U.S. Cl. ...................................... 30/178; 30/316; 30/363
[58] Field of Search .................. 30/363, 119, 178, 316

[56] References Cited

U.S. PATENT DOCUMENTS

| | | | |
|---|---|---|---|
| 422,666 | 3/1890 | Tull et al. | 30/178 X |
| 787,348 | 4/1905 | Hansen | 30/178 X |
| 2,612,686 | 10/1952 | Wagner | 30/178 |
| 4,102,045 | 7/1978 | Bergh | 30/178 X |
| 4,391,042 | 7/1983 | Sunderland | 30/316 |

Primary Examiner—Frank T. Yost
Assistant Examiner—Michael D. Folkerts
Attorney, Agent, or Firm—William M. Hobby, III

[57] ABSTRACT

A cutting tool for cutting an opening in a colostomy stoma wafer barrier is provided having first and second lever handles, each having a lever jaw portion connected together for the handles to open and close the jaws. One jaw has a removably attached annular cutting blade attached to the jaw portion while the other jaw has a cutting block attached thereto having an annular cutting groove formed therein and shaped for the annular cutting blade to enter, to thereby cut a piece of material placed between the annular cutting blade and the cutting block. The cutting block is loosely attached and may have a plurality of annular cutting grooves for different sized blades. Each annular cutting blade may have an alignment pin to fit in an alignment notch in the jaw. One lever handle has a slot formed therein for the other lever handle to fit therethrough and is pinned through the slot walls and through the other handle.

5 Claims, 1 Drawing Sheet

CUTTING TOOL FOR COLOSTOMY WAFER

BACKGROUND OF THE INVENTION

The present invention relates to a cutting tool, and specifically to a tool for cutting a circular opening in a wafer barrier for attaching a colostomy pouch.

A colostomy is an opening or stoma made in the wall of the abdomen of a patient to which an opening in the colon (ostomy) is attached. Thereafter, the contents of the colon can be eliminated through the stoma instead of through the rectum or anus. The operation is called an ileostomy when the opening is through the lower part of the small intestines or ileum. A colostomy operation requires the attaching of a barrier to the skin around the opening and which may be called a wafer, such as a pectin or a kayara or other wafers, and which is used for attaching a stoma pouch. Colostomy pouches can then be held to the wafer and to the stoma by magnets, or by colostomy belts.

The present invention relates to a tool for quickly and accurately cutting a hole in the wafer barrier for attaching to the skin of the patient around the stoma. Inasmuch as the barrier material might be a relatively heavy co-polymer material having a thick adhesive layer, a tool is need which can accurately cut through the thick material with an opening for the attachment member for attaching a colostomy pouch.

A typical ostomate appliance can be seen in the U.S. Pat. No. 4,344,433 to Smith, and facilitates the connection between the stoma and the ostomy. A typical prior art punch which inserts a square blade into a square groove can be seen in U.S. Pat. No. 3,721,144 to Yamamori and typical levered plier-like cutting tools can be seen in button-hole cutters in U.S. Pat. No. 97,996 and in U.S. Pat. No. 79,418 both to Walker. These cutting tools are for cutting button holes having a generally straight line with a specified length and cut against a fixed anvil. In addition to these Patents, prior art paper punches are typically leveraged punches including solid cylindrical cutting blades which enters a punching cylinder for punching holes in the edge of paper sheets.

SUMMARY OF THE INVENTION

The present invention relates to a colostomy wafer cutting tool which has a first jaw member, including a levered handle and a levered jaw portion and a second jaw member having a lever handle and a lever jaw portion with the first and second jaw members being attached to the handle and jaw portions thereof so that the jaws can be actuated with the handles, similar to the action of a pair of pliers or scissors. A removably attached annular cutting blade is attached to the lever jaw portion of the first jaw member and a cutting block is attached to the second jaw member lever jaw portion, and has an annular cutting groove therein shaped for an annular cutting blade attached to the first jaw member to fit therein to coact therewith for cutting a piece of flat material placed between the annular cutting blade and cutting block. The cutting block may have a plurality of annular grooves for accepting different diameter cutting blades. The first jaw member jaw portion may also have an alignment opening for receiving an alignment pin attached to the removably attached annular cutting blade. The first jaw member and second jaw member can be connected by having a slot formed in one jaw member with the other jaw member extending therethrough and being pinned together through the slot walls and second jaw member. The cutting block may be loosely riveted to the second jaw member jaw portion with a small amount of play to facilitate the cutting.

BRIEF DESCRIPTION OF THE DRAWINGS

Other objects, features and advantages of the present invention will be apparent from the written description and the drawings in which.

DESCRIPTION OF THE PREFERRED EMBODIMENT

Figure 1:
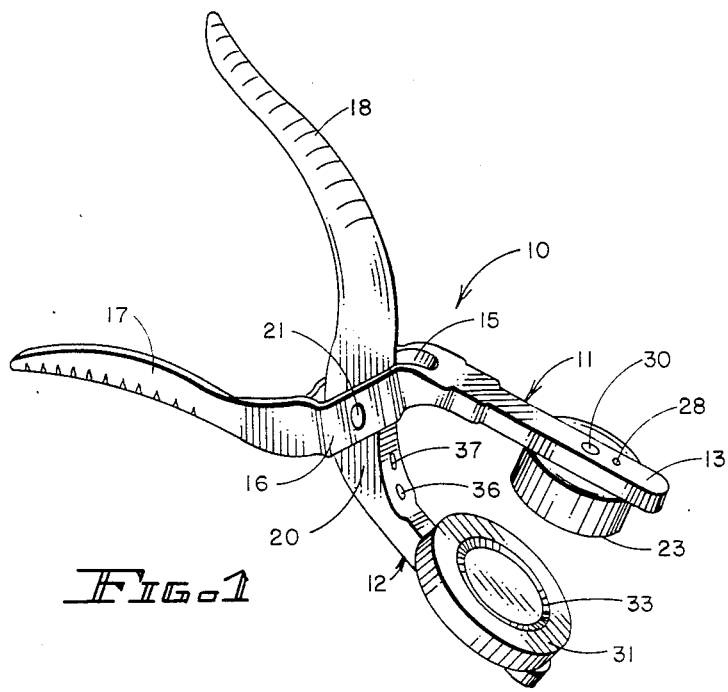
FIG. 1 is a perspective view of a colostomy wafer cutting tool in accordance with the present invention.
Figure 2:
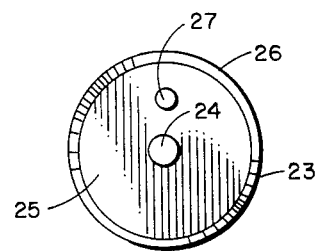
FIG. 2 is a rear elevation of the cutting blade of FIG. 1.

Referring to the drawings, a colostomy wafer cutting tool 10 is shown having a first jaw member 11 and a second jaw member 12. The first jaw member has a jaw portion 13 and a handle portion 17 with a slot 15 in the center portion 16. The second jaw member 12 has a jaw portion 14 and a levered handle portion 18 with a center portion 20 passing through the slot 15 of the jaw member 11. Jaw members 11 and 12 are connected with a pin 21 through the center portion 16, slot 15 walls and through the center portion 20 of the jaw member 12, so that the tool works like a levered pliers or scissors mechanism such that by moving the handle portions 17 and 18, the jaw portions 13 and 14 are moved and are given a mechanical advantage by the length of the handles 17 and 18 being greater than the length of the jaw members 13 and 14 from the center pin 21. A spring may be wrapped around the pin 21 and biased against the jaw members 11 and 12 to bias the handle portions 17 and 18 apart for ease in use. The jaw members 13 and 14 are, nevertheless, more elongated than a typical pliers type action because of the necessity of centering a piece of material for a colostomy wafer 22 in the proper position for cutting the hole therein. The jaw member 13 has an annular cutting blade 23 attached thereto with a threaded fastener 24 through the bottom 25 of the cutting blade 23 having the cutting edge 26 therearound. The cutting blade 23 is a cylindrical blade having a sharp cutting edge 26 and a bottom 25 and an alignment pin 27 attached to the bottom 25. The alignment pin fits in an opening 28 in the jaw portion 13 of the lever jaw 11, while the threaded fastener 24 fits in a threaded opening 30 in the jaw member 13. The jaw member 12 has a cutting block 31 attached thereto such as with a rivet 32 and has an annular cutting groove 33 formed therein. The rivet 32 may be a threaded fastener member but attaches through an opening 34 in the jaw member 14. The annular cutting groove 33 is made to coact with the annular cutting blade 23 to give a generally scissors type cutting action by the one passing into the other.

Figures 4, 5:
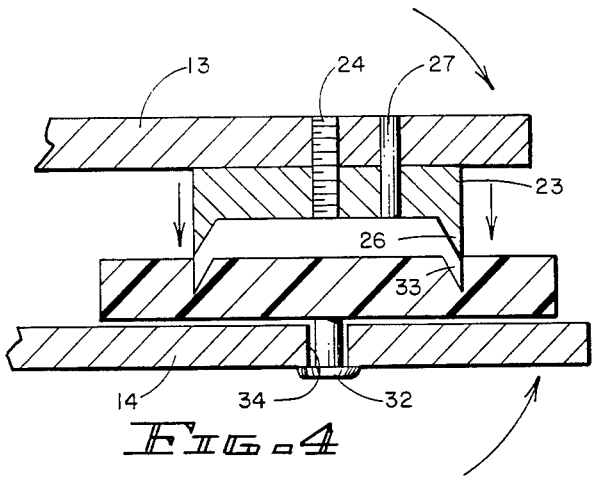
FIG. 4 is a sectional view taken through the cutting portion of the cutting tool of FIG. 1 showing the blades being closed.
FIG. 5 is a sectional view in accordance with FIG. 4 having the blades closed.
Figure 6:
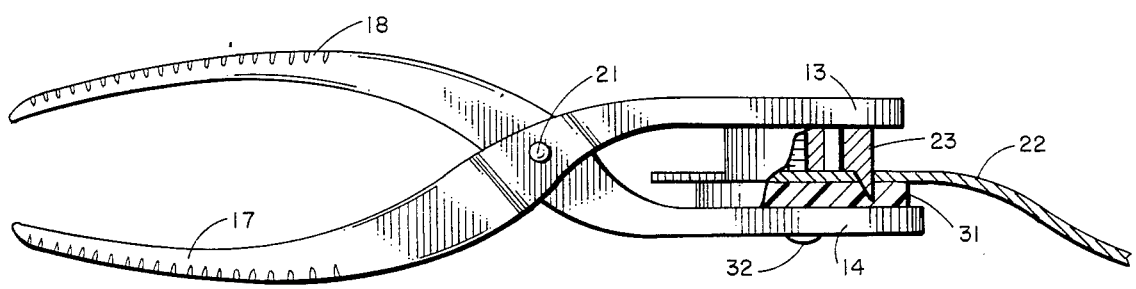
FIG. 6 is a side elevation view with a portion cutaway of the cutting of FIGS. 1 through 5 cutting an opening in a piece of material.

As seen in FIGS. 4, 5 and 6, pressing the handles 17 and 18 with a piece of wafer material 22 between the annular cutting blade 23 and cutting block 31 allows the handles to be closed thereby closing the blade 23 onto the cutting block 33. Mechanical advantage is obtained by the lever action of the handles 17 and 18 levered on the pin 21 with the shorter jaws 13 and 14, as the annular blade 23 approaches the block. As seen in FIG. 4, the blade 23 exactly aligns with the cutting groove 33 of the block 31. A small amount of play is provided b the rivet 32 attached to the block 31 to assure alignment. The cutting blade then enters the cutting block annular cutting groove 33 shown in FIG. 5 which would allow it to cut a perfect circular opening through the heavy wafer material 22.

Figure 3:
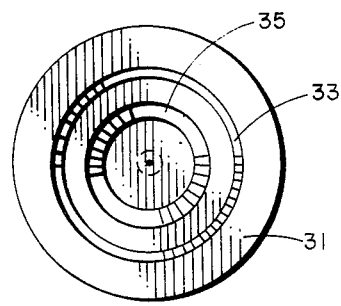
FIG. 3 is a front elevation of the cutting block of FIG. 1.

As shown in FIG. 3, a second annular groove 35 may be formed in the cutting block 31 so that the blade 23 can rapidly be changed in size for different operations or patients without having to change the cutting block 31. Changing the cutting blade is rapidly accomplished by the alignment pin 27 sliding in the alignment opening 28 and then the threaded fastener or screw 24 being threaded into the threaded opening 30.

It should be clear at this time that a colostomy wafer cutting tool has been provided for making rapid cuts in wafer material. The cutting also may be seen to have a pair of threaded openings 36 and 37 in FIG. 1 which may be used for attaching a stop alignment edge for precisely aligning the center of the wafer for cutting the openings therein.

Accordingly, the present invention is not to be construed as limited to the forms shown which are to be considered illustrative rather than restrictive.

I claim:
1. A colostomy wafer cutting tool comprising:
 a first jaw member including a lever handle and a lever jaw portion, said first and second jaw members being movable attached together between the handle and jaw portions thereof, whereby the jaws can be actuated with said lever handle portions;
 a removably attached annular cutting blade attached to the lever jaw portion of said first jaw member, said removably attached annular cutting blade bottom having an alignment pin attached thereto and said first jaw member lever jaw portion having an opening therein for receiving said alignment pin;
 a cutting block attached to the second jaw member lever jaw portion and having an annular cutting groove therein shaped for said annular cutting block to enter to thereby cut a piece of material placed between said annular cutting blade and said cutting block, said cutting block being loosely attached to said second jaw member lever jaw portion whereby said cutting block can slightly tilt to the angle of said annular cutting blade; and
 said second jaw member having a threaded opening therein for attaching an alignment stop thereto.

2. A wafer cutting tool in accordance with claim 1 in which said removably attached annular cutting blade is attached with a threaded fastening member.

3. A wafer cutting tool in accordance with claim 2 in which said removably attached annular cutting blade is a cylindrical shaped blade having a cutting edge and having a bottom having an opening therein for attaching said threaded fastener therethrough.

4. A wafer cutting tool in accordance with claim 1 in which said cutting block has a plurality of annular cutting grooves formed therein for accepting different size removably attached annular cutting blades whereby said opening size can be altered by changing the removably attached annular cutting blade.

5. A wafer cutting tool in accordance with claim 1 in which said first jaw member has a slot therein between the lever handle portion and the lever jaw portion and said second jaw member extends through said slot in said first jaw member and is pinned thereto.

* * * * *